United States Patent [19]

Besson

[11] Patent Number: 4,766,230

[45] Date of Patent: Aug. 23, 1988

[54] PREPARATION OF ARYLAMINOALUMINUMS

[75] Inventor: Bernard Besson, Villeurbanne, France

[73] Assignee: Rhone-Poulenc Chimie de Base, Courbevoie, France

[21] Appl. No.: 919,683

[22] Filed: Oct. 16, 1986

[30] Foreign Application Priority Data

Oct. 16, 1985 [FR] France ............................. 85 15544

[51] Int. Cl.$^4$ ............................................... C07F 5/06
[52] U.S. Cl. ................................................... 556/176
[58] Field of Search ........................................ 556/176

[56] References Cited

U.S. PATENT DOCUMENTS

| Re. 29,389 | 9/1977 | Merkl | 556/176 X |
|---|---|---|---|
| 2,655,524 | 10/1953 | Sowa | 556/176 |
| 2,814,646 | 11/1957 | Kolka | 556/176 X |
| 3,208,986 | 9/1965 | Mazzanti et al. | 556/176 X |
| 3,649,693 | 3/1972 | Napolitano | 556/176 X |
| 3,654,331 | 4/1972 | Klopfer | 556/176 |
| 3,856,841 | 12/1974 | Merkl | 556/176 X |

OTHER PUBLICATIONS

Chemical Abstracts 56: 3498i (1962).
Chemical Abstracts 70: 87879k (1969).

*Primary Examiner*—Paul F. Shaver
*Attorney, Agent, or Firm*—Burns, Doane, Swecker & Mathis

[57] ABSTRACT

The arylaminoaluminums, well adopted as catalysts for the ortho-alkylation of aromatic amines with an olefin, are facilely prepared by reacting at least one aromatic amine with metallic aluminum in the presence of a catalytically effective amount of iodine, or precursor compound thereof which generates elemental iodine under the conditions of reaction.

11 Claims, 1 Drawing Sheet

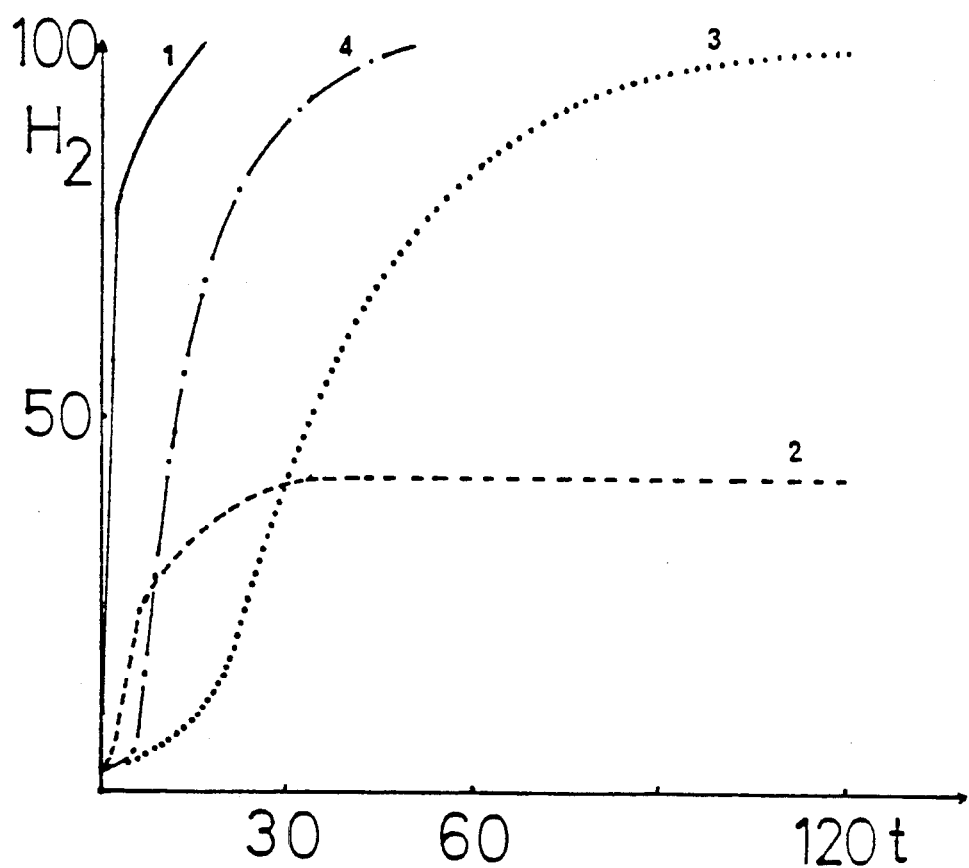

PREPARATION OF ARYLAMINOALUMINUMS

BACKGROUND OF THE INVENTION

1. Field of the Invention

The present invention relates to the preparation of arylaminoaluminums.

2. Description of the Prior Art

Arylaminoaluminums are known materials which are especially useful as catalysts in the ortho-alkylation of aromatic amines with olefins.

Thus, the alkylation of an aromatic amine with olefins, at a temperature of 200° to 400° C. in the presence of aluminum, is described in U.S. Pat. No. 2,762,845. The amine must contain at least one hydrogen atom on the nitrogen atom and at least one hydrogen atom on the aromatic nucleus. If the aluminum-based catalyst can be used in any suitable form, 1 to 2% of aluminum relative to the amine to be alkylated is generally used, and, in practice, the amine and the aluminum source are first brought to a temperature of from 300° to 350° C. When the evolution of hydrogen, caused by the reaction of the aromatic amine with the catalyst to form the corresponding tri(arylamino)aluminum compound is complete, the olefin is then added. The pressure, when the latter is a gas, is on the order of 50 to 300 bar.

The reaction product is then isolated by distillation, either with steam or under vacuum.

Similarly, in *Angew. Chem.*, 68, No. 11, page 387 (1956), referring briefly to the ethylation of aniline in the presence of aluminum, the author points out that aromatic diamines may also be ethylated in the presence of trianilinoaluminum.

Various methods for preparing a trianilinoaluminum type catalyst are also reported in U.S. Pat. No. 2,814,646, one of the simplest consisting of directly contacting the aromatic amine with the aluminum. Also reported in this patent are certain of the advantages associated with the use of a preformed catalyst, in particular the absence of hydrogen evolution which enables a greater partial pressure of the gaseous reagents to be obtained during the actual performance of the alkylation reaction.

It is also known to this art, from U.S. Pat. No. 3,275,690 and the aforesaid *Angew. Chem.* article, that mercuric chloride is an accelerator of the reaction of aniline with aluminum.

In my laboratory, it has now been observed that the reaction of aniline with aluminum is possible in the absence of accelerator, provided that the reaction is carried out at a high temperature, e.g., greater than 280° C., which necessitates carrying out the reaction in reactors which are resistant to pressure and which is consequently unsatisfactory from an economic point of view.

We have also observed that the subject reaction can be carried out at atmospheric pressure, at the reflux temperature of aniline (approximately 180° C.), in the presence of mercuric chloride, if the reaction is rapid and quantitative. If, however, the paste thus obtained is catalytically active in the alkylation of toluenediamines, for example, it is difficult to handle and the presence of mercuric chloride in such paste tends to contaminate the alkylation products ultimately obtained. Moreover, the cost of mercuric chloride adversely affects the overall cost-effectiveness of the process.

Thus, serious need exists in this art for a novel process for the synthesis of tri(arylamino)aluminums which avoids the disadvantages and drawbacks of the prior efforts in this field.

SUMMARY OF THE INVENTION

Accordingly, a major object of the present invention is the provision of such novel improved process for the preparation of tri(arylamino)aluminums, by reacting, at elevated temperature, at least one aromatic amine with metallic aluminum, and wherein the reaction is carried out in the presence of a catalytically effective amount of iodine, or in the presence of a compound which generates iodine under the conditions of the reaction (an "iodine precursor").

DETAILED DESCRIPTION OF THE PREFERRED EMBODIMENTS OF THE INVENTION

More particularly according to the present invention, the tri(arylamino)aluminums consistent herewith advantageously have the general formula (I):

wherein $R_1$, $R_2$ and $R_3$, which may be identical or different, are each a hydrogen atom or a phenyl radical; $Ar_1$, $Ar_2$ and $Ar_3$, which also may be identical or different, are each a phenyl radical, a phenyl radical substituted by one or more $C_1$–$C_4$ alkyl radicals, or by at least one halogen atom, or by an —$NH_2$ group, or a naphthyl radical optionally substituted by said $C_1$–$C_4$ alkyl radicals, halogen atoms or amino group.

Preferably, $R_1$, $R_2$ and $R_3$ are identical and are a hydrogen atom.

Preferably, $Ar_1$, $Ar_2$ and $Ar_3$ are identical and advantageously are a phenyl radical which may contain a $C_1$–$C_4$ alkyl substituent.

These compounds are obtained by reacting at least one aromatic amine of the formula $Ar_i$—$NR_iH$, in which i may be 1, 2 or 3, and $R_i$ and $Ar_i$ have the definitions of $R_1$ to $R_3$ and $Ar_1$ to $Ar_3$. Exemplary of the aromatic amines suitable for carrying out the process according to the invention, the following are representative: aniline, ortho-, meta- or para-monoethylanilines, naphthylamine, toluidines, xylidines, o-chloroaniline, diphenylamine, m-phenylenediamine, benzidine, 3,5-dimethylaniline, 3,6-diethylaniline, and mixtures thereof.

Primary amines (those wherein $R_i$ is hydrogen, and i=1 to 3), and more particularly those which are liquid at ambient temperature (on the order of 25° C.) are preferably used. Most typically, a single amine or mixture of isomers of such amine is used. Among the primary amines, it is preferred to use those corresponding to the formula $Ar_iNH_2$ in which $Ar_i$ is a phenyl radical which may contain a $C_1$–$C_4$ alkyl substituent. Aniline and ortho-, meta- or para-monoethylanilines and mixtures of aniline and ortho-ethylaniline are more particularly suitable.

The aluminum metal may be used in the reaction in any form. Powders of variable particle size, shavings or ingots are equally suitable for carrying out the process according to the invention.

The reaction is carried out in the presence of iodine, or an iodine compound which is capable of producing iodine in situ under the conditions of the reaction (iodine precursor). For this purpose, inorganic or organic derivatives such as the following compounds are representative:

$FeI_2$, $FeI_3$, $CoI_2$ and more generally any iodide of a metal which is less electropositive than aluminum, $CH_2I_2$, $C_2H_4I_2$ and various compositions or combinations known to those skilled in this art for producing iodine, such as the combination of an iodide and a thiosulfate.

Preferably, iodine itself is used.

The amounts of aromatic amine(s) and aluminum, respectively, may vary over wide limits. However, it is preferable to carry out the reaction with at least three amine equivalents per aluminum atom. A large excess of amine is advantageously used in order to obtain a fluid phase which can be transferred under cold conditions when the tri(arylamino)aluminum is to be used as the catalyst for the o-alkylation of an aromatic amine, as mentioned hereinbefore.

In general, this ease of handling will be achieved when the aluminum content of the liquid phase does not exceed 3.5% by weight, which corresponds to an aluminum "concentration" on the order of 1.2 mole per kilogram.

The amount of catalyst (iodine) to be used may also vary over wide limits. An optimum is determined for each amine used, taking into account the contradictory conditions below:

The reaction rate is an increasing function of the amount of iodine added, as well as the amount of iodinated by-products which are likely to be coproduced.

In general, an $I_2$ concentration of from $10^{-4}$ to $5.10^{-2}$ mat.g/kg (mat.g=milliatomgram) provides satisfactor results.

The reaction is carried out at atmospheric pressure, the temperature obviously depending on the reactivity of the aromatic amine employed, or on that of the amine mixture used.

This temperature typically ranges from 100° to 350° C.

When the reaction is carried out using aniline, a temperature in the vicinity of the boiling point of the latter proves very satisfactory.

Upon completion of the reaction, the product obtained is collected, and can then be used, where appropriate, as the catalyst in the ortho-alkylation of aromatic amines with an olefin.

In order to further illustrate the present invention and the advantages thereof, the following specific examples are given, it being understood that same are intended only as illustrative and in nowise limitative.

EXAMPLES

EXAMPLE 1

(comparative)

The following materials were charged into a round-bottomed flask fitted with a reflux condenser:

(i) 0.9 g (33.3 mmol) of aluminum powder;
(ii) 17.4 g (187.2 mmol) of aniline;
(iii) 25 mg ($9.2.10^{-2}$ mmol) of $HgCl_2$.

The contents of the flask were then heated to 180° C. (reflux temperature of aniline). The gases evolved during the reaction were collected. The reaction began slightly before the reflux temperature of aniline was reached. The gas evolution was rapid and quantitative in 20 minutes.

After cooling the reaction product, a very viscous grey paste was obtained.

This paste was catalytically active without adding an optional co-catalyst (Lewis acid) in the alkylation reaction of toluenediamine with ethylene, under the conditions described in Example 38 of U.S. Pat. No. 3,275,690.

EXAMPLE 2

(comparative)

The procedure of Example 1 was repeated, but omitting the addition of mercuric chloride.

The reaction was slow to commence and it was not quantitative.

EXAMPLE 3

The procedure of Example 1 was repeated, but using $8.10^{-3}$ mmol of iodine in place of the mercuric chloride. The time lapse between the onset of reflux and the completion of gas evolution was 2 hours; the volume of hydrogen evolved represented 100% of the theoretical volume.

EXAMPLE 4

The procedure of Example 1 was repeated, but using $8.10^{-2}$ mmol of iodine in place of the mercuric chloride. The time lapse between the onset of reflux and the completion of gas evolution was ¾ of an hour; the volume of hydrogen evolved represented 100% of the theoretical volume.

The trianilinoaluminums obtained in Example 3 and in Example 4 were excellent catalysts in the aforedescribed alkylation reaction.

In each of the Examples 1 to 4, the volume of hydrogen evolved was measured (NTPC) as a function of the reaction time (at 180° C.) and the evolution of gases was calculated on the basis of the theoretical volume. The curves numbered 1 to 4 plotted on the graph of the FIGURE of Drawing were thus obtained; along the ordinate, the amount of hydrogen evolved is expressed as a percentage of the theoretical volume and along the abscissa, the reaction time in minutes.

DESCRIPTION OF THE DRAWING

Curve 1 corresponds to Example 1, carried out using $9.2.10^{-2}$ mmol of $HgCl_2$ (control trial).

Curve 2 corresponds to Example 2, carried out without catalyst (control trial).

Curve 3 corresponds to Example 3, carried out using $8.10^{-3}$ mmol of iodine.

Curve 4 corresponds to Example 4, carried out using $8.10^{-2}$ mmol of iodine.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a tri(arylamino)aluminum, comprising reacting at least one aromatic amine with metallic aluminum, at elevated temperature, in the presence of a catalytically effective amount of iodine or precursor thereof.

2. The process as defined by claim 1, wherein said catalytically effective amount of iodine ranges from $10^{-4}$ to $5.10^{-2}$ mat.g/kg.

3. The process as defined by claim 1, wherein the aluminum content in the liquid phase is less than about 3.5% by weight.

4. The process as defined by claim 1, wherein the temperature of reaction ranges from 100° C. to 350° C.

5. The process as defined by claim 1, wherein the catalyst is elemental iodine.

6. The process as defined by claim 1, wherein said at least one aromatic amine has the formula, $Ar_i$—$NR_iH$, wherein i=1, 2 or 3; $Ar_1$, $Ar_2$ and $Ar_3$, which may be identical or different, are each a phenyl radical, a phenyl radical substituted by one or more $C_1$-$C_4$ alkyl radicals or halogen atoms, or an —$NH_2$ group, a naphthyl radical, or a naphthyl radical substituted by one or more $C_1$-$C_4$ alkyl radicals or halogen atoms, or an amino group; and $R_i$ is a hydrogen atom or a phenyl radical.

7. The process as defined by claim 6, wherein said formula $R_i$ is hydrogen.

8. The process as defined by claim 6, wherein said formula $Ar_i$ is a phenyl radical, or a phenyl radical bearing at least one $C_1$-$C_4$ alkyl substituent.

9. The process as defined by claim 1, wherein said aromatic amine comprises aniline, ortho-ethylaniline, or mixture thereof.

10. The process as defined by claim 1, wherein the temperature of reaction is the boiling temperature, at atmospheric pressure, of the aromatic amine.

11. A process for the preparation of a tri(arylamino)aluminum, comprising reacting at least one aromatic amine with metallic aluminum, said metallic aluminum present in an amount in the liquid phase of less than about 3.5% by weight, at a temperature of from about 100° C. to 350° C., in the presence of from about $10^{-4}$ to about $5.10^{-1}$ mat.g/kg of iodine or precursor thereof, wherein said at least one aromatic amine has the formula, $Ar_i$—$NR_iH$, wherein i=1, 2 or 3; $Ar_1$, $Ar_2$ and $Ar_3$, which may be identical or different, are each a phenyl radical, or a phenyl radical bearing at least one $C_1$-$C_4$ alkyl substituent, and $R_1$, $R_2$ and $R_3$ are hydrogen.

* * * * *